United States Patent [19]

Mayer et al.

[11] Patent Number: 5,071,470
[45] Date of Patent: Dec. 10, 1991

[54] HERBICIDAL 1,3,5-TRIAZIN-2-YLAMINOCARBONYLAMINO-SULFONYLBENZOIC ESTERS

[75] Inventors: Horst Mayer, Ludwigshafen; Gerhard Hamprecht, Weinheim; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 494,671

[22] Filed: Mar. 16, 1990

[30] Foreign Application Priority Data

Mar. 21, 1989 [DE] Fed. Rep. of Germany ....... 3909146

[51] Int. Cl.$^5$ ................... C07D 251/16; A01N 43/66
[52] U.S. Cl. ......................................... 71/93; 544/211
[58] Field of Search .............................. 544/211; 71/93

[56] References Cited

U.S. PATENT DOCUMENTS 4,383,113 5/1983 Levitt ........................................ 71/93
4,661,147 4/1987 Dumas ...................................... 71/92
4,897,108 1/1990 Damas ...................................... 71/93

FOREIGN PATENT DOCUMENTS 0030138 6/1981 European Pat. Off. .
0057546 8/1982 European Pat. Off. .
0007687 3/1983 European Pat. Off. .

Primary Examiner—John M. Ford
Attorney, Agent, or Firm—Keil & Weinkauf

[57] ABSTRACT

[[(1,3,5-Triazin-2-yl)aminocarbonyl]aminosulfonyl]benzoic esters of the general formula I

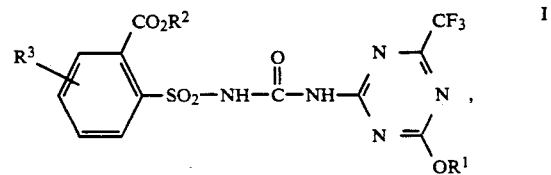

wherein $R^1$ and $R^2$ are methyl or ethyl, and $R^3$ is hydrogen, fluorine or chlorine, agriculturally useful salts thereof, processes for their manufacture, and their use.

5 Claims, No Drawings

HERBICIDAL 1,3,5-TRIAZIN-2-YLAMINOCARBONYLAMINO-SULFONYLBENZOIC ESTERS

The present invention relates to 1,3,5-triazin-2-ylaminocarbonylaminosulfonylbenzoic esters of the general formula I

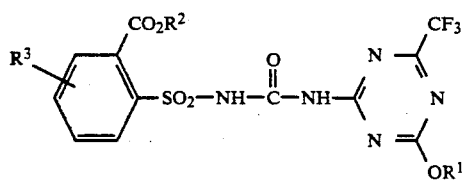

where $R^1$ and $R^2$ are methyl or ethyl, and $R^3$ is hydrogen, fluorine or chlorine.

The present invention also relates to a process for the preparation of the compounds I and to the use thereof as herbicides.

EP-A 7687, EP-A 30 138 and EP-A 57 546 relate to sulfonylureas which have a herbicidal action and whose general formula embraces the compounds I defined above.

Whereas the nearest structures described in EP-A 57 546 are only 1,3,5-triazine N-oxide derivatives I'

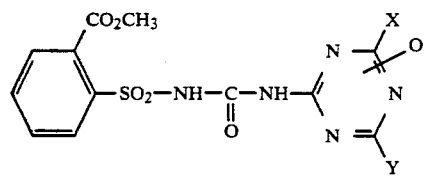

in which the meanings of the radicals are, inter alia:

X and Y are, independently of one another, methyl or methoxy, and

O is oxygen in the 1, 3 or 5 position of the triazinyl ring, the emphasis in EP-A 30 138 is on variation of the ester ortho to the sulfonamide moiety. Haloalkyl substituents in the triazine moiety are not described in this citation.

Only in EP-A 7687 is there a description of a triazinyl derivative with a haloalkyl radical (I").

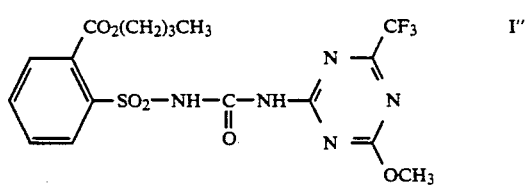

The present invention has the object of synthesizing sulfonylureas which have improved properties compared with known representatives of this class of herbicides.

In accordance with this object, we have found the 1,3,5-triazin-2-ylaminocarbonylaminosulfonylbenzoic esters of the formula I defined above.

The sulfonylureas of the formula I according to the invention can be obtained by a variety of routes described in the literature. Particularly advantageous routes (A, B and C) are explained in detail hereinafter by way of example.

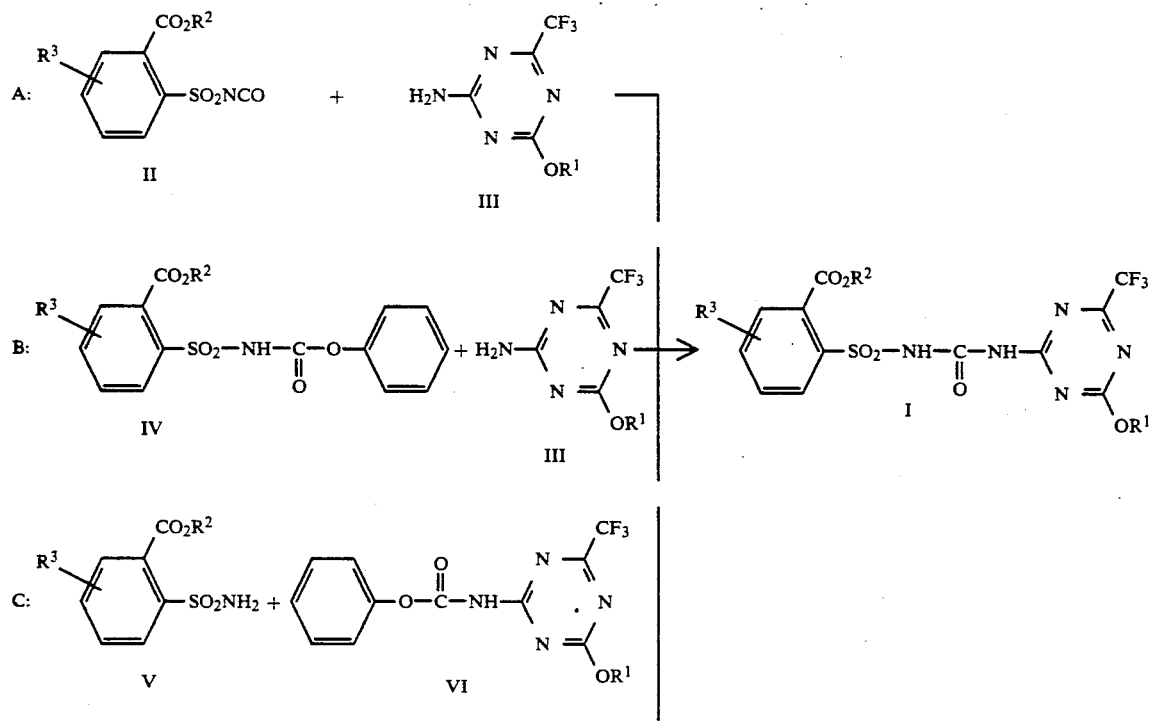

-continued

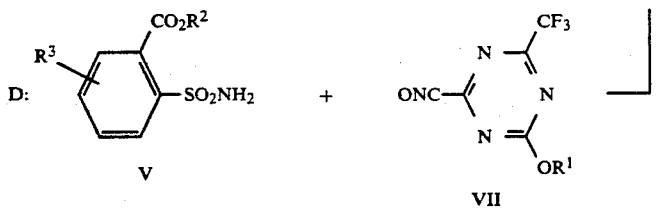

A: A sulfonyl isocyanate II is reacted in a conventional manner (EP-A 162 723) with approximately the stoichiometric amount of a 2-amino-1,3,5-triazine derivative of III at from 0° to 120° C., preferably 10° to 100° C. The reaction can be carried out under atmospheric or superatmospheric pressure (up to 50 bar), preferably under 1 to 5 bar, continuously or batchwise.

It is expedient to use solvents or diluents which are inert under the particular reaction conditions. Examples of suitable solvents are halohydrocarbons, especially chlorohydrocarbons, e.g. tetrachloroethylene, 1,1,2,2- or 1,1,1,2-tetrachloroethane, dichloropropane, methylene chloride, dichlorobutane, chloroform, chloronaphthalane, dichloronaphthalene, tetrachloromethane, 1,1,1- or 1,1,2-trichloroethane, trichloroethylene, pentachloroethane, o-, m-, p-difluorobenzene, 1,2-dichloroethane, 1,1-dichlorethane, 1,2-cis-dichloroethylene, chlorobenzene, fluorobenzene, bromobenzene, iodobenzene, o-, m-, p-dichlorobenzene, o-, p-, m-dibromobenzene, o-, m-, p-chlorotoluene, 1,2,4-trichlorobenzene; ethers, e.g. ethyl propyl ether, methyl tert-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole, b,b'-dichlorodiethyl ether; nitrohydrocarbons such as nitromethane, nitroethane, nitrobenzene, o-, m-, p-chloronitrobenzene, o-nitrotoluene; nitriles such as acetonitrile, butyronitrile, isobutyronitrile, benzonitrile, m-chlorobenzonitrile; aliphatic or cycloaliphatic hydrocarbons, e.g. heptane, pinane, nonane, o-, m-, p-cymene, petroleum fractions within a boiling range from 70° to 190° C., cyclohexane, methylcyclohexane, decalin, petroleum ether, hexane, ligroin, 2,2,4-trimethylpentane, 2,2,3-trimethylpentane, 2,3,3-trimethylpentane, octane; esters, e.g. ethyl acetate, ethyl acetoacetate, isobutyl acetate; amides, e.g. formamide, methylformamide, dimethylformamide; ketones, e.g. acetone, methyl ethyl ketone and mixtures thereof. The solvent is expediently used in an amount of from 100 to 2000% by weight, preferably from 200 to 700% by weight, based on the starting material II.

The compound II required for the reaction is generally employed in an approximately equimolar amount (e.g. from 0 to 20% above or below equimolar) based on the starting material III. The starting material III can be initially introduced in one of the abovementioned diluents and then the starting material II can be added.

However, the process for preparing the novel compounds is expediently carried out in such a way that the starting material II is initially introduced, where appropriate in one of the abovementioned diluents, and then the starting material III is added.

The reaction is completed by stirring, after the addition of the components, for 20 minutes to 24 hours at from 0° to 120° C., preferably 10° to 100° C., in particular 20° to 80° C.

It is possible and advantageous to add a reaction accelerator in the form of a tertiary amine, e.g. pyridine, a-, b- or c-picoline, 2,4- or 2,6-lutidine, 2,4,6-collidine, p-dimethylaminopyridine, trimethylamine, triethylamine, tri(n-propyl)amine, 1,4-diazabicyclo[2.2.2]octane [DABCO] or 1,8-diazabicyclo[5.4.0]undec-7-ene in an amount of from 0.01 to 1 mole per mole of starting material II.

The final product I is isolated from the reaction mixture in a conventional manner, e.g. after removal of the solvent by distillation or directly by filtration with suction. The residue which remains can then be washed with water or dilute acid to remove basic impurities. However, the residue can also be dissolved in a solvent which is immiscible with water and be washed as described. This results in the desired final products in pure form, but, if necessary, they can be purified by recrystallization, stirring in an organic solvent which dissolves the impurities, or chromatography.

This reaction is preferably carried out in acetonitrile, methyl tert-butyl ether, toluene or methylene chloride in the presence of from 0 to 100 mol-equivalents, preferably 0 to 50 mol-equivalents, of a tertiary amine such as 1,4-diazabicyclo[2.2.2]octane or triethylamine.

B: An appropriate sulfonylcarbamate of the formula IV is reacted in a conventional manner (EP-A 120 814) in an inert organic solvent at from 0° to 120° C., preferably 10° to 100° C., with a 2-amino-1,3,5-triazine derivative III. It is possible to add bases such as tertiary amines, which increases the reaction rate and improves the product quality.

Examples of bases suitable for this purpose are tertiary amines as indicated under A, especially triethylamine or 1,4-diazabicyclo[2.2.2]octane, in an amount of from 0.01 to 1 mole per mole of starting material IV.

It is expedient to use as solvent those indicated under A. The solvent is used in an amount of from 100 to 2000% by weight, preferably from 200 to 700% by weight, based on the starting material IV.

The compound IV required for the reaction is generally employed in an approximately equimolar amount (e.g. from 0 to 20% above or below equimolar) based on the particular starting material III. The starting material IV can be initially introduced in one of the abovementioned diluents, and then the starting material III can be added.

However, the starting material can also be initially introduced in one of the said solvents or diluents, and the sulfonylcarbamate IV can be added.

In both cases it is possible to add a base as catalyst before or during the reaction.

The final product I can be obtained from the reaction mixture in a conventional manner as indicated under A.

C: A sulfonamide of the formula V is reacted in a conventional manner (EP-A 141 777) in an inert organic solvent with approximately the stoichiometric amount of a phenyl carbamate VI at from 0° to 120° C., preferably 20° to 100° C. The reaction can be carried out under atmospheric or superatmospheric pressure (up to 50 bar), preferably under 1 to 5 bar, continuously or batchwise.

It is possible to add bases such as tertiary amines, which increase the reaction rate and improve the product quality. Bases suitable for this are those indicated under A, especially triethylamine, 2,4,6-collidine, 1,4-diazabicyclo[2.2.2]octane [DABCO] or 1,8-diazabicyclo[5.4.0]undec-7-ene (DBU), in an amount of from 0.01 to 1 mole per mole of starting material V.

It is expedient to use the solvents or diluents indicated under A.

The solvent is used in an amount of from 100 to 2000% by weight, preferably from 200 to 700% by weight, based on the precursor V.

The compound V required for the reaction is generally employed in an approximately equimolar amount (e.g. from 0 to 20% above or below equimolar) based on the starting material VI. The starting material VI can be initially introduced in one of the abovementioned diluents and then the starting material can be added.

However, the starting material V can also be initially introduced in one of the said solvents and then the carbamate VI can be added. In both cases it is possible to add one of the said bases as catalyst before or during the reaction.

The reaction is completed by stirring, after the addition of the components, for 20 minutes to 24 hours at from 0° to 120° C., preferably 10° to 100° C., in particular 20° to 80° C.

The sulfonylureas of the formula I are isolated from the reaction mixture by conventional methods as described under A.

D: A sulfonamide of the formula V is reacted in a conventional manner (EP-A 234 352) in an inert organic solvent with approximately the stoichiometric amount of an isocyanate VII at from 0° to 150° C., preferably 10° to 100° C. The reaction can be carried out under atmospheric or superatmospheric pressure (up to 50 bar), preferably under 1 to 5 bar, continuously or batchwise.

It is possible to add, before or during the reaction, bases such as tertiary amines which increase the reaction rate and improve the product quality. Bases suitable for this purpose are those indicated under A, especially triethylamine or 2,4,6-collidine, in an amount of from 0.01 to 1 mole per mole of starting material V.

It is expedient to use the solvents indicated under A. The solvent is employed in an amount of from 100 to 2000% by weight, preferably from 200 to 700% by weight, based on the precursor V.

The compound V required for the reaction is generally employed in an approximately equimolar amount (e.g. from 0 to 20% above or below equimolar) based on the precursor VII. The starting material VII can be initially introduced in one of the said diluents and then the starting material V can be added.

However, the sulfonamide can also be initially introduced, and then the isocyanate VII can be added.

The reaction is completed by stirring, after addition of the components, for 20 minutes to 24 hours at 0° to 120° C., preferably 10° to 100° C., in particular 20° to 80° C.

The final product I can be obtained from the reaction mixture in a conventional manner as described under A.

The sulfonyl isocyanates of the formula II used as precursors were obtained by literature, or similar, methods (e.g. EP-A 7687). The sulfonylcarbamates of the formula IV were prepared by known, or similar, reactions (e.g. EP-A 120,814). However, it is also possible to convert sulfonyl isocyanates of the formula II in a smooth reaction with phenol in a solvent such as ether or acetonitrile into the carbamates of the formula IV.

Carbamates of the formula VI can be obtained by known, or similar, reactions (e.g. EP-A 141 777), but they can also be prepared from the corresponding isocyanates of the formula VII by reaction with phenol.

The salts of the compounds I can be obtained in a conventional manner (EP-A 304 282, U.S. Pat. No. 4,599,421). They are obtained by deprotonation of the corresponding sulfonylureas in water or an inert organic solvent at from $-80°$ C. to 120° C., preferably 0° C. to 60° C., in the presence of a base.

Examples of suitable bases are alkali metal or alkaline earth metal hydroxides, hydrides, oxides or alcoholates such as sodium, potassium and lithium hydroxide, sodium methanolate, ethanolate and tert.-butanolate, sodium and calcium hydride and calcium oxide.

Examples of suitable solvents are, besides water, also alcohols such as methanol, ethanol and tert-butanol, ethers such as tetrahydrofuran and dioxane, acetonitrile, dimethylformamide, ketones such as acetone and methyl ethyl ketone, and halohydrocarbons.

The deprotonation can be carried out under atmospheric or superatmospheric pressure up to 50 bar, preferably under atmospheric pressure to 5 bar superatmospheric pressure.

The sulfonamides required as starting materials of the formula V can be prepared from the corresponding anthranilic esters by the Meerwein reaction and subsequent reaction with ammonia (Houben-Weyl, 9,557 et seq. (1955)).

The 2-amino-4-methoxy-6-trifluoromethyl-1,3,5-triazine and 2-amino-4-ethoxy-6-trifluoromethyl-1,3,5-triazine precursors are known from the literature (Yakugaku Zasshi 95,499 (1975)).

The compounds I, and herbicidal agents containing them, and their environmentally compatible alkali metal and alkaline earth metal salts, have an excellent action on injurious plants in crops such as wheat, without damaging the crop plant, an effect which occurs particularly at low application rates. They may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

The compounds I are particularly suitable for the preparation of solutions, emulsions, pastes and oil dispersions to be sprayed direct. Examples of suitable inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient.

Examples of formulations are as follows:

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 2 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 3 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 4 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 5 is intimately mixed with 97 parts by weight of particulate kaolin. A dust is obtained containing 3% by weight of the active ingredient.

VII. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 6 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3.0, preferably 0.01 to 1.0, kg of active ingredient per hectare.

In view of the numerous application methods possible, the compounds according to the invention, or the agents containing them, may be used in a large number of crops for removing unwanted plants. Those which follow are given by way of example:

| Botanical name | Common name |
|---|---|
| *Allium cepa* | onions |
| *Ananas comosus* | pineapples |
| *Arachis hypogaea* | peanuts |
| | (groundnuts) |

| Botanical name | Common name |
| --- | --- |
| *Asparagus officinalis* | asparagus |
| *Avena sativa* | oats |
| *Beta vulgaris* spp. altissima | sugarbeets |
| *Beta vulgaris* spp. rapa | fodder beets |
| *Beta vulgaris* spp. esculenta | table beets, red beets |
| *Brassica napus* var. napus | rapeseed |
| *Brassica napus* var. napobrassica | swedes |
| *Brassica napus* var. rapa | turnips |
| *Brassica rapa* var. silvestris | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum*, *Gossypium herbaceum*, *Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (*N. rustica*) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. tuberosum | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (s. vulgare) | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Triticum durum* | durum wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the triazinyl-substituted sulfonylureas of the formula I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, phenyloxy- or heteroaryloxyphenylpropionic acid derivatives (salts, esters, amides), etc.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

Examples of the synthesis of compounds I follow.

1) Methyl 2-(4-trifluoromethyl-6-methoxy-1,3,5-triazin-2-ylaminocarbonylaminosulfonyl)benzoate

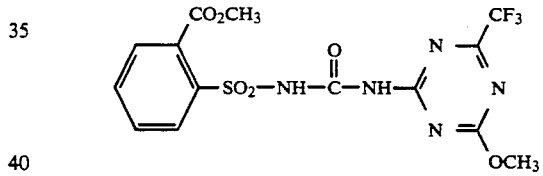

9.3 g (39 mmol) of 2-methoxycarbonylbenzenesulfonyl isocyanate were added at 25° C. to a solution of 5.0 g (26 mmol) of 2-amino-4-methoxy-6-trifluoromethyl-1,3,5-triazine in 80 ml of acetonitrile. The resulting mixture was heated at 70° C. for 5 hours. After the reaction mixture had cooled to 25° C., it was diluted with methylene chloride and washed with 2N sodium hydroxide solution. The aqueous phase was acidified and then extracted with methylene chloride. The organic phase was worked up in a conventional manner, and chromatography yielded 6.8 g (60% of theory) of the desired compound of melting point 165°-167° C.

2) Methyl 2-(4-trifluoromethyl-6-ethoxy-1,3,5-triazin-2-ylaminocarbonylaminosulfonyl)benzoate

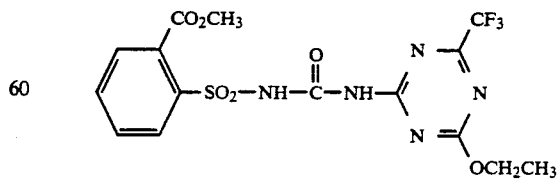

Under the conditions described in Example 1, 3.3 g (30% of theory) of the desired product of melting point 164°-168° C. were obtained from 5.0 g (24 mmol) of 2-amino-4-ethoxy-6-trifluoromethyl-1,3,5-triazine and 7.0 g (29 mmol) of 2-methoxycarbonylbenzenesulfonyl isocyanate in 80 ml of acetonitrile.

3) Methyl 4-chloro-2-(4-trifluoromethyl-6-methoxy-1,3,5-triazin-2-ylaminocarbonylaminosulfonyl)benzoate.

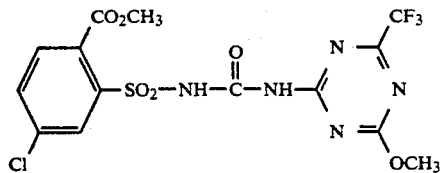

A solution of 5.0 g (26 mmol) of 2-amino-4-trifluoromethyl-6-methoxy-1,3,5-triazine, 7.1 g (26 mmol) of 4-chloro-2-methoxycarbonylbenzenesulfonyl isocyanate and 100 ml of acetonitrile was stirred at 25° C. for 72 h. The solvent was then removed by distillation under reduced pressure at 40° C., and the resulting residue was recrystallized from ethyl acetate/ether. This resulted in 6.5 g (53% of theory) of the title compound of melting point 148°–150° C.

4) Sodium salt of methyl 2-(4-trifluoromethyl-6-methoxy-1,3,5-triazin-2-ylaminocarbonylaminosulfonyl)benzoate

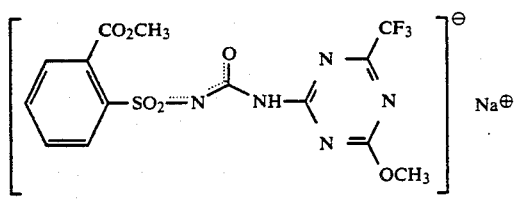

A solution of 2.0 g (4.6 mmol) of the compound prepared in Example 1, 0.25 g (4.6 mmol) of sodium methanolate and 50 ml of methanol were stirred at 25° C. for 1 h. The solvent was then removed by distillation under reduced pressure at elevated temperature. The desired salt was obtained in quantitative yield, melting point 175° C. (decomposition).

5) Methyl 2-(4-trifluoromethyl-6-methoxy-1,3,5-triazin-2-ylaminocarbonylaminosulfonyl)benzoate

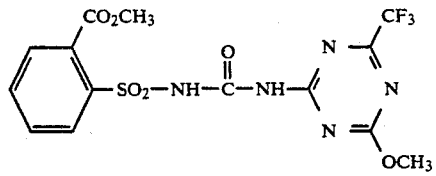

a) 2-Isocyanato-4-methoxy-6-trifluoromethyl-1,3,5-triazine

A solution of 30.0 g of 2-amino-4-methoxy-6-trifluoromethyl-1,3,5-triazine (0.154 mol) and 76.2 g of oxalyl chloride (0.6 mol) in 225 ml of toluene was refluxed for 4 hours. Initially there was vigorous evolution of gas but this rapidly diminished. After the reaction was complete the mixture was fractionated under reduced pressure. 24.8 g of the product were obtained as a mobile, colorless oil of boiling point 67°–70° C. (0.1 mbar) (73% of theory).

b)
A solution of 2.2 g of methyl 2-aminosulfonylbenzoate (10 mmol) and 2.2 g of 2-isocyanato-4-methoxy-6-trifluoromethyl-1,3,5-triazine in 20 ml of acetonitrile was stirred at 22° to 25° C. for 15 hours. The reaction product was purified as described for Example 1.

This resulted in 2.4 g (55% of theory) of the product of melting point 165°–167° C.

6) Methyl 2-(4-trifluoromethyl-6-methoxy-1,3,5-triazin-2-ylaminocarbonylaminosulfonyl)benzoate

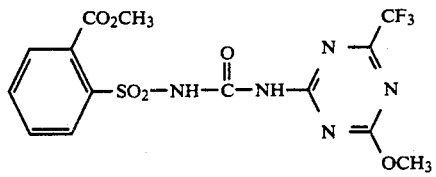

a) 2-Methoxy-4-phenoxycarbonylamino-6-trifluoromethyl-1,3,5-triazine 4.3 g of phenol (45 mmol) were added at 25° C. to a solution of 100 g of 2-isocyanato-4-methoxy-6-trifluoromethyl-1,3,5-triazine (45 mmol) in 50 ml of acetonitrile. After addition of 30 mg of 1,4-diazobicyclo[2.2.2]octane, the mixture warmed to 40° C. and a slight yellow coloration appeared. The mixture was stirred for a further 15 min and the solvent was removed under reduced pressure at 50° C. The almost colorless residue crystallized overnight. This resulted in 14.0 g of the title compound (98% of theory).

$^1$H of the NMR spectrum (CDCl$_3$, 250 MHz, TMS, 25° C.), d (ppm): 8.3 bar (NH); 7.31 m (2H ar); 7.24 m (1H ar); 7.16 m (2H ar); 4.12 s (3H OCH$_3$).

b)
A solution of 2.3 g of 2-methoxy-4-phenoxycarbonylamino-6-trifluoromethyl-1,3,5-triazine (7.3 mmol), 1.6 g of 2-methoxycarbonylbenzenesulfonamide (7.3 mmol), 1.1 g of 1,8-diazabicyclo[5.4.0]undec-7-ene (7.3 mmol) in 10 g of acetonitrile was stirred at 25° C. for 10 min, under reflux for 5 min and then at 25° C. for 2 h. The oily residue after removal of the solvent under reduced pressure at 50° C. was taken up in 200 ml of ethyl acetate. The solution was shaken with 40 ml of 4N NaOH and then at 0° C. with 50 ml of 4N HCl.

The organic phase was separated off, washed until neutral with saturated brine, dried over Na$_2$SO$_4$ and concentrated. The oily residue crystallized on stirring with 200 ml of an ether/pentane mixture (1/1 V:V). The product was filtered and dried at 40° C. under reduced pressure.

1.5 g (47% of theory) of the title compound were obtained, which was identical to the compound obtained by route A.

7) Methyl 4-fluoro-2-(4-methoxy-6-trifluoromethyl-1,3,5-triazin-2-ylaminocarbonylaminosulfonyl)benzoate

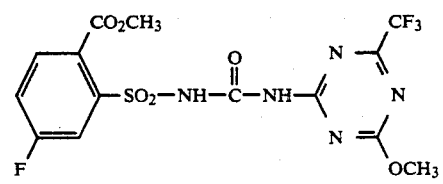

11.0 g of a solution of 4.9 g of 4-fluoro-2-methoxycarbonylbenzenesulfonyl isocyanate (19 mmol) and 1,2-dichloroethane were added dropwise at 25° C. to a solution of 3.7 g of 2-amino-4-methoxy-6-trifluoromethyl-1,3,5-triazine (19 mmol). The mixture was stirred at 25° C. for 65 h, the volatiles were removed under reduced pressure at 60° C. and the solid residue was vigorously stirred with 200 ml of diethyl ether. The product was filtered off, washed with ether and dried. This resulted in 4.4 g of the title compound (51% of theory) of melting point 153°–157° C.

8) Methyl 2-(4-methoxy-6-trifluoromethyl-1,3,5-triazin-2-ylaminocarbonylaminosulfonyl)benzoate

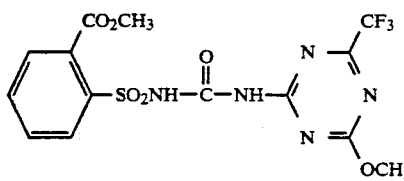

294.5 g of 2-amino-4-methoxy-6-trifluoromethyl-1,3,5-triazine (1.52 mol) were added at 25° C. to a solution of 366.2 g of 2-methoxycarbonylbenzenesulfonyl isocyanate (1.52 mol) in 280 ml of acetonitrile. The mixture was stirred at this temperature for 15 h.

The precipitate was filtered off with suction, washed with a little acetonitrile and stirred 3 times with 300 ml of a diethyl ether/hexane mixture (1:1 V:V) each time. The residue was isolated and dried. This resulted in 432.0 g (65% of theory) of the title compound (melting point 165°–167° C.). The mother liquor was concentrated to one half of the volume and stored at 25° C. for 16 hours. The precipitate was isolated, stirred 3 times with 500 ml of a diethyl ether/hexane mixture (1:1 V:V) each time, again isolated and dried. This resulted in a further 92.5 g of the title compound (14% of theory) (melting point 165°–167° C.).

9) Calcium salt of methyl 2-(4-trifluoromethyl-6-methoxy-1,3,5-triazin-2-ylaminocarbonylaminosulfonyl)benzoate

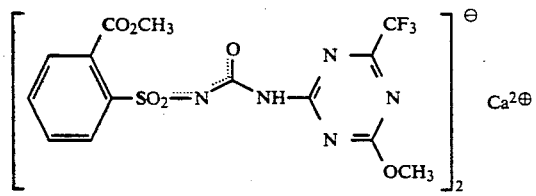

A solution of 2.0 g (4.6 mmol) of the compound prepared in Example 1), 0.20 g (4.8 mmol) of calcium hydride and 50 ml of methanol was stirred at 25° C. for 10 h. A homogeneous solution was initially formed, and then the product separated out as a solid. The usual isolation resulted in 0.6 g (14% of theory) of the desired calcium salt of melting point 175°–178° C. (decomposition).

The active ingredients additionally listed in Table 1 below may be obtained analogously:

TABLE 1

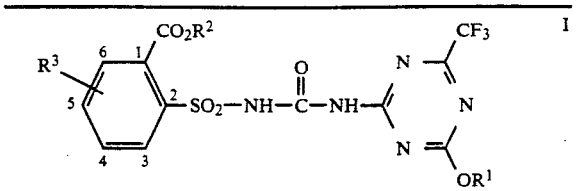

| Active ingr. | R¹ | R² | R³ | mp [°C.] |
|---|---|---|---|---|
| 1 | CH₃ | CH₃ | H | 165–167 |
| 2 | CH₂CH₃ | CH₃ | H | 164–168 |
| 3 | CH₂CH₃ | CH₃ | 6-F | 173–175 |
| 4 | CH₃ | CH₃ | 5-Cl | 144–145 |
| 5 | CH₃ | CH₃ | 6-Cl | 153–155 |
| 6 | CH₃ | CH₃ | 6-F | 166–168 |
| 7 | CH₃ | CH₃ | 4-Cl | 148–150 |
| 8 | CH₃ | CH₃ | 4-F | 153–157 |
| 9 | CH₃ | CH₃ | H | 175 (Na salt) |
| 10 | CH₃ | CH₃ | H | 175–178 (Ca salt) |

USE EXAMPLES

The herbicidal action of [[(1,3,5-triazin-2-yl)aminocarbonyl]aminosulfonyl]benzoates of the formula I on the growth of test plants is shown in the following greenhouse experiments.

The vessels employed were plastic flowerpots having a volume of 300 cm³ and filled with a sandy loam containing about 3.0% humus. The seeds of the test plants were sown shallow, and separately, according to species.

For the postemergence treatment, either plants sown directly in the pots and grown there were used, or plants which were cultivated separately as seedlings and were transplanted to the vessels a few days before treatment.

Depending on growth form, the plants were grown to a height of 3 to 15 cm before being treated with the active ingredients, which were suspended or emulsified in water and sprayed through finely distributing nozzles. The application rate for postemergence treatment was 0.06 kg/ha.

The pots were set up in the greenhouse, species from warmer climates in warmer areas (20° to 35° C.) and species from moderate climates at 10° to 20° C. The experiments were run for from 2 to 4 weeks. During this time the plants were tended and their reactions to the various treatments assessed.

The assessment scale was 0 to 100, 100 denoting nonemergence or complete destruction of at least the visible plant parts, and 0 denoting no damage or normal growth.

The plants used in the greenhouse experiments were *Amaranthus retroflexus, Cyperus iria, Galium aparine,* Ipomoea spp., *Polygonum persicaria, Triticum aestivum* and Veronica spp.

The compounds of Examples 1 and 2, applied postemergence at a rate of 0.06 kg/ha, combated unwanted broadleaved plants very well, and were excellently tolerated by wheat plants.

Tables 2 and 3 below contain the results of biological investigations in which the active ingredients according to the invention are compared with prior art compounds.

The prior art compounds used for comparison purposes were sulfonylureas A and B disclosed in EP-A 7,687:

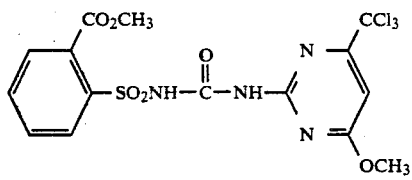

A

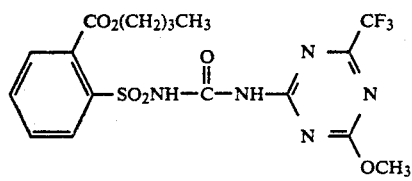

B

TABLE 1

Comparision of the herbicidal action of compound no. 1 with that of compound A disclosed in EP-A 7,687 at a postemergence application rate of 0.015 kg/ha in the greenhouse

| Test plants | Damage [%] | |
|---|---|---|
| | Compound 1 | A |
| Triticum aestivum | 0 | 0 |
| Amaranthus retroflexus | 85 | 60 |
| Galium aparine | 98 | 10 |
| Ipomea spp. | 80 | 50 |
| Polygonum persicaria | 80 | 30 |
| Veronica spp. | 100 | 20 |

TABLE 2

Comparison of the herbicidal action of compound no. 2 with that of compound B disclosed in EP-A 7,687 at a postemergence application rate of 0.06 kg/ha in the greenhouse

| Test plants | Damage [%] | |
|---|---|---|
| | Compound 2 | B |
| Triticum aestivum | 0 | 0 |
| Cyperus iria | 100 | 0 |
| Amaranthus retroflexus | 98 | 0 |
| Galium aparine | 95 | 0 |
| Ipomoea spp. | 100 | 10 |
| Polygonum persicaria | 100 | 0 |
| Veronica spp. | 100 | 0 |

We claim:

1. A [[(1,3,5-triazin-2-yl)aminocarbonyl]aminosulfonyl]benzoic ester of the formula I

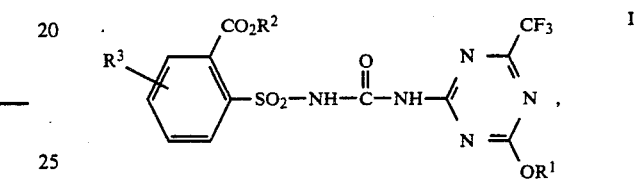

where $R^1$ and $R^2$ are methyl or ethyl, and $R^3$ is hydrogen, fluorine or chlorine, and agriculturally useful salts thereof.

2. A compound of the formula I as defined in claim 1, wherein $R^1$ is $CH_3$, $R^2$ is $CH_3$ and $R^3$ is H.

3. A compound of the formula I as defined in claim 1, wherein $R^1$ is $CH_2CH_3$, $R^2$ is $CH_3$ and $R^3$ is H.

4. A herbicidal composition containing a herbicidally effective amount of a [[(1,3,5-triazin-2-yl)-aminocarbonyl]-aminosulfonyl]-benzoic ester of the formula I as set forth in claim 1, or an agriculturally useful salt thereof, and conventional carriers therefor.

5. A process for combating the growth of unwanted plants, wherein a herbicidally effective amount of a [[(1,3,5-triazin-2-yl)-aminocarbonyl]-aminosulfonyl]-benzoic ester of the formula I as set forth in claim 1, or an agriculturally useful salt thereof, is allowed to act on the plants and/or their habitat.

* * * * *